(12) United States Patent
Faux et al.

(10) Patent No.: US 11,690,748 B2
(45) Date of Patent: Jul. 4, 2023

(54) ORTHOSIS BRACE COMPRISING REEL-BASED LACING SYSTEM

(71) Applicant: FOOTSCIENTIFIC INC., Draper, UT (US)

(72) Inventors: Jonathan Robert Faux, Draper, UT (US); Chris Hughes, Draper, UT (US); Gary Moore, Draper, UT (US)

(73) Assignee: Footscientific Inc., Draper, UT (US)

( * ) Notice: Subject to any disclaimer, the term of this patent is extended or adjusted under 35 U.S.C. 154(b) by 436 days.

(21) Appl. No.: 16/905,591

(22) Filed: Jun. 18, 2020

(65) Prior Publication Data

US 2021/0393428 A1    Dec. 23, 2021

(51) Int. Cl.
*A61F 5/01*    (2006.01)
*A43B 7/20*    (2006.01)

(52) U.S. Cl.
CPC .............. *A61F 5/0113* (2013.01); *A43B 7/20* (2013.01)

(58) Field of Classification Search
CPC .... A61F 5/0113; A61F 5/0111; A61F 5/0109; A61F 5/0106; A61F 5/0104; A61F 5/0102; A61F 5/01; A43B 7/20; A43B 7/19; A43B 7/18; A43B 7/00
See application file for complete search history.

(56) References Cited

U.S. PATENT DOCUMENTS

| | | | |
|---|---|---|---|
| 5,445,602 A * | 8/1995 | Grim | A61F 5/012 602/6 |
| 8,986,235 B2 * | 3/2015 | Weaver, II | A61F 5/0111 602/61 |
| 9,427,350 B1 * | 8/2016 | Clements | A61F 5/01 |
| 9,717,619 B2 * | 8/2017 | Dodin | A61F 5/0102 |
| 2012/0004587 A1 * | 1/2012 | Nickel | A61F 5/028 602/5 |
| 2012/0246974 A1 * | 10/2012 | Hammerslag | A43C 11/004 36/83 |
| 2014/0276318 A1 * | 9/2014 | Faux | A61F 5/0109 602/28 |
| 2014/0276320 A1 * | 9/2014 | Faux | A61F 5/0113 602/28 |

FOREIGN PATENT DOCUMENTS

| | | | | |
|---|---|---|---|---|
| CA | 3036219 A1 * | 3/2018 | | A61F 5/0111 |
| CN | 108135330 A * | 6/2018 | | A43C 1/00 |
| DE | 102018201019 A1 * | 8/2018 | | A41D 13/06 |
| EP | 2783661 A1 * | 10/2014 | | A61F 5/0113 |
| WO | WO-2010117723 A2 * | 10/2010 | | A61F 5/0111 |
| WO | WO-2012003396 A2 * | 1/2012 | | A43C 1/003 |

OTHER PUBLICATIONS

International Search Report and Written Opinion Received from PCT Application No. PCT/US21/37929, dated Oct. 21, 2021, 11 Pages.

* cited by examiner

*Primary Examiner* — Tarla R Patel
(74) *Attorney, Agent, or Firm* — Terrence J. Edwards; TechLaw Ventures, PLLC (57) ABSTRACT

Orthosis brace comprising reel-based lacing system for alleviating foot drop experienced by a user. A device includes a support configured to wrap around at least a portion of a lower leg of a user and a lace support attached to the support and configured to receive a lace. The device includes a reel-based fastener attached to the support, wherein the reel-based fastener comprises a reel for receiving the lace and adjusting a tautness of the lace.

20 Claims, 9 Drawing Sheets

ORTHOSIS BRACE COMPRISING REEL-BASED LACING SYSTEM

TECHNICAL FIELD

The disclosure relates generally to orthoses systems and devices and particularly relates to orthoses configured for treating and alleviating conditions relating to feet.

BACKGROUND

Foot drop (also referred to as "drop foot") is a condition in which a front part of a person's foot drops involuntarily. Foot drop is caused by various conditions, including weakness of the forefoot, injury to the peroneal nerve, paralysis of muscles in the anterior portion of the lower leg, or a variety of other conditions such as stoke, multiple sclerosis, Charcot-Marie-Tooth disease, and others. Foot drop may be temporary or permanent and can affect one foot or both of an individual's feet.

Foot drop can adversely affect an individual's ability to walk. A person with food drop may drag his or her toes along the ground when walking or lift his or her knee higher than normal when walking to prevent the foot from dragging, resulting in what is commonly referred to as "steppage gait." These complications can decrease the mobility of persons affected by foot drop.

Various orthoses are available for treating foot drop. However, these orthoses known in the art are often difficult to set up and adjust. Many orthoses require specialized or modified shoes. The orthoses known in the art are not convenient because they are complex to put on and adjust, can be exceptionally heavy, and lack flexibility. Therefore, there is a need for adjustable, and easy-to-use orthoses to assist individuals experiencing foot drop.

In light of the foregoing, disclosed herein are systems, methods, and devices for raising a forefoot of a person's foot. Such systems, methods, and devices as disclosed herein can be used to alleviate the conditions associated with foot drop and other conditions that may be addressed by adjusting an angle of the foot relative to the lower leg.

BRIEF DESCRIPTION OF THE DRAWINGS

Non-limiting and non-exhaustive implementations of the present disclosure are described with reference to the following figures, wherein like reference numerals refer to like parts throughout the various views unless otherwise specified. Advantages of the present disclosure will become better understood with regard to the following description and accompanying drawings where.

DETAILED DESCRIPTION

Disclosed herein are systems, methods, and devices for alleviating conditions associated with foot drop and other conditions that may be addressed by adjusting an angle of the foot relative to the lower leg. For the sake of simplicity, such an orthosis may be referred to herein as an "orthosis brace." A orthosis brace may be configured to exert an upward force on a foot-receiving member such as an item of footwear or some other foot-receiving member configured to be worn on an individual's foot.

An embodiment of the disclosure is an orthosis brace for addressing foot drop. The orthosis brace includes a support configured to wrap around at least a portion of a lower leg of a user and a lace support attached to the support and configured to receive a lace. The orthosis brace further includes a reel-based fastener attached to the support, wherein the reel-based fastener comprises a reel for receiving the lace and adjusting a tautness of the lace.

Before the structures, systems, and methods for integrating a surveillance system with a digital lockbox are disclosed and described, it is to be understood that this disclosure is not limited to the particular structures, configurations, process steps, and materials disclosed herein as such structures, configurations, process steps, and materials may vary somewhat. It is also to be understood that the terminology employed herein is used for the purpose of describing particular embodiments only and is not intended to be limiting since the scope of the disclosure will be limited only by the appended claims and equivalents thereof.

In describing and claiming the subject matter of the disclosure, the following terminology will be used in accordance with the definitions set out below.

It must be noted that, as used in this specification and the appended claims, the singular forms "a," "an," and "the" include plural referents unless the context clearly dictates otherwise.

As used herein, the terms "comprising," "including," "containing," "characterized by," and grammatical equivalents thereof are inclusive or open-ended terms that do not exclude additional, unrecited elements or method steps.

As used herein, the phrase "consisting of" and grammatical equivalents thereof exclude any element or step not specified in the claim.

As used herein, the phrase "consisting essentially of" and grammatical equivalents thereof limit the scope of a claim to the specified materials or steps and those that do not materially affect the basic and novel characteristic or characteristics of the claimed disclosure.

Reference will now be made in detail to the exemplary embodiments, examples of which are illustrated in the accompanying drawings. Wherever possible, the same reference numbers are used throughout the drawings to refer to the same or like parts. It is further noted that elements disclosed with respect to embodiments are not restricted to only those embodiments in which they are described. For example, an element described in reference to one embodiment or figure, may be alternatively included in another embodiment or figure regardless of whether or not those elements are shown or described in another embodiment or figure. In other words, elements in the figures may be interchangeable between various embodiments disclosed herein, whether shown or not.

Figure 1:
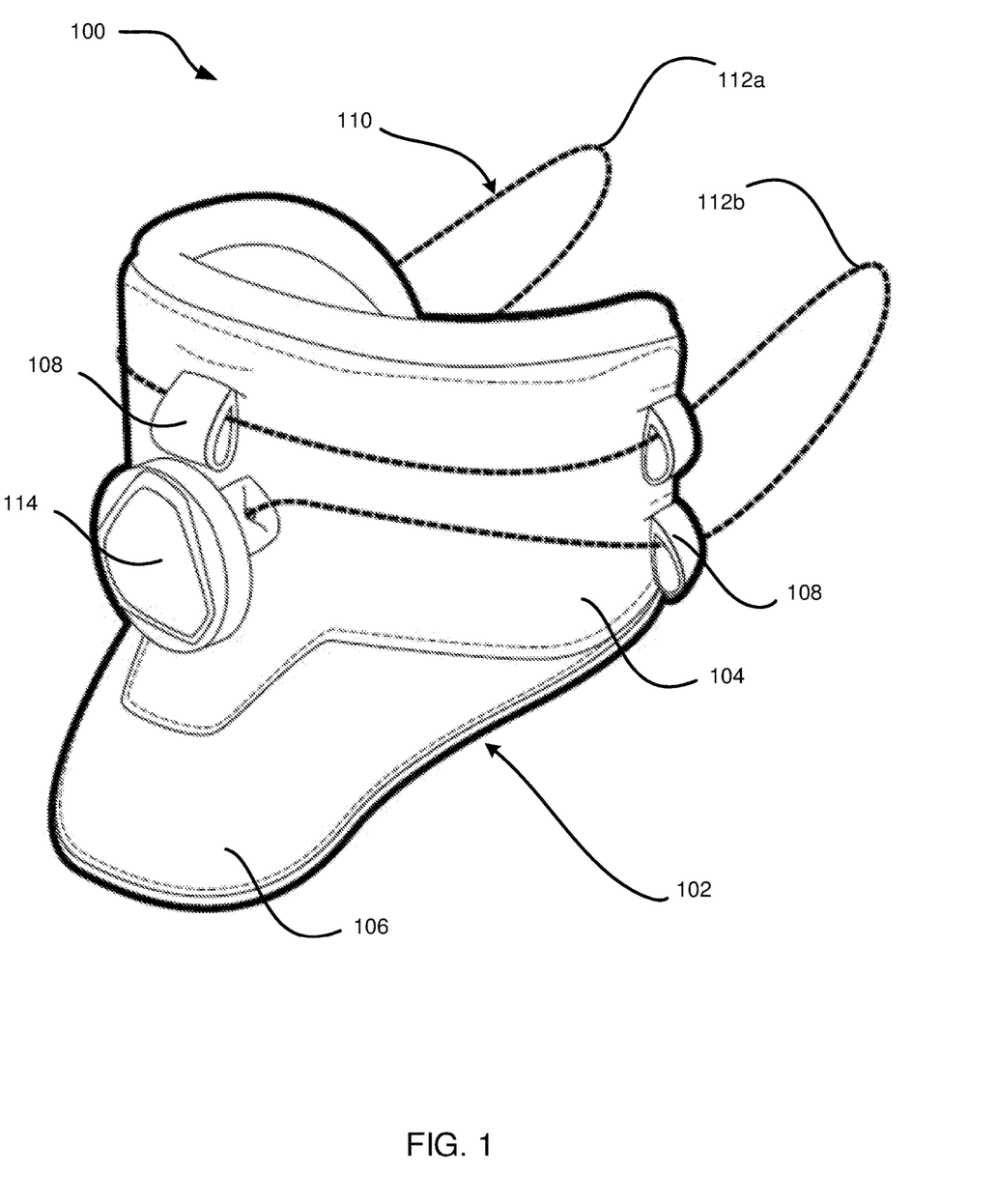
FIG. 1 is a perspective view of an orthosis brace for correcting foot drop and other conditions that may be alleviated by adjusting an angle of the foot relative to the lower leg, according to one embodiment.

Referring now to the figures, FIG. 1 is a perspective view of an orthosis brace 100 for correcting foot drop and other conditions that may be alleviated by adjusting an angle of the foot relative to the lower leg. The orthosis brace 100 includes a support 102 for encircling the orthosis brace 100 around a lower portion of a user's leg. The support 102 includes an ankle support portion 104 and a counter support portion 106. The orthosis brace 100 further includes lace supports 108 for providing a tab, loop, eyelet, hole, or other opening for receiving a lace and holding the lace in place. The orthosis brace 100 includes a lace 110 comprising a first shoe connector 112a and a second shoe connector 112b. The orthosis brace 100 includes a reel-based fastener 114 configured for receiving the lace 110 and winding and/or releasing the lace from a reel for tightening and/or loosening the orthosis brace 100.

The support 102 is configured to wrap around a lower portion of a user's leg. In an embodiment, the support 102 wraps around the posterior or dorsal side of the lower portion of the user's leg. In such an embodiment, the support 102 may contact the user's leg at a region where the Achilles tendon is located within the user's leg. The support 102 may be constructed for a rigid, semi-rigid, or flexible material. In an embodiment, the support 102 comprises an inner frame constructed of rigid plastic, metal, or some other rigid material. The support 102 may additionally be covered in a soft material including a foam cushion or padding along with a fabric wrapping. The support 102 may be constructed of a flexible or non-rigid material that wraps around the user's lower leg and forms to the shape of the user's lower leg.

The ankle support portion 104 of the support 102 is configured to wrap around the posterior or dorsal side of the lower portion of the user's leg. When the orthosis brace 100 is in use, the ankle support portion 104 may be located at or near the region of the user's leg that comprises the Achilles tendon. The ankle support portion 104 may comprise a rigid or semi-rigid inner material covered with a lining to provide cushion and support to the user.

The counter support portion 106 of the support 102 is located below the ankle support portion 104 when the orthosis brace 100 is in use on a user's leg. The counter support portion 106 is configured to come in contact with or be located near the counter of a shoe when the orthosis brace 100 is in use. The counter of a shoe (may also be referred to as a "heel counter") is located at the rear of a shoe and provide support to the wearer's foot. The counter support portion 106 may be configured to press against or rest upon the counter of a shoe. The counter support portion 106 may also be configured to extend outward relative to the ankle support portion 104 to provide clearance for the counter of a shoe. The counter support portion 106 may be constructed of any suitable rigid or semi-rigid material and may be covered with padding or lining to increase comfort for the user.

The lace supports 108 provide a means to secure the laces 110 of the orthosis brace 100. The lace support 108 may be attached to the support 102 and may be constructed of any suitable material. In an embodiment as illustrated in FIG. 1, the lace support 108 may include a loop of fabric or other material configured for receiving the lace 110 therethrough. The lace supports 108 of the orthosis brace 100 may include one or more of a loop, tab, eyelet, hole, tunnel, channel, or other means for receiving a lace 110 and holding the lace 110 in place while still permitting the lace 110 to slide through the lace support 108.

The lace 110 is configured for tightening the orthosis brace 100 and providing a means for attaching the orthosis brace 100 to a shoe or other device. The lace 110 may comprise any suitable lacing device that may be used with footwear or orthoses. In an embodiment, the lace 110 is constructed of twine or line that can withstand relatively high tension forces. In an embodiment, the lace 110 is constructed of a line such as fishing line and may be constructed from one or more fibers. The one or more fibers of the line may be made of nylon, polyvinylidene fluoride, polyethylene, and others. In an embodiment, the lace 110 is configured for being received by the reel-based fastener 114 and winding in and out of the reel-based fastener 114.

Figure 3:
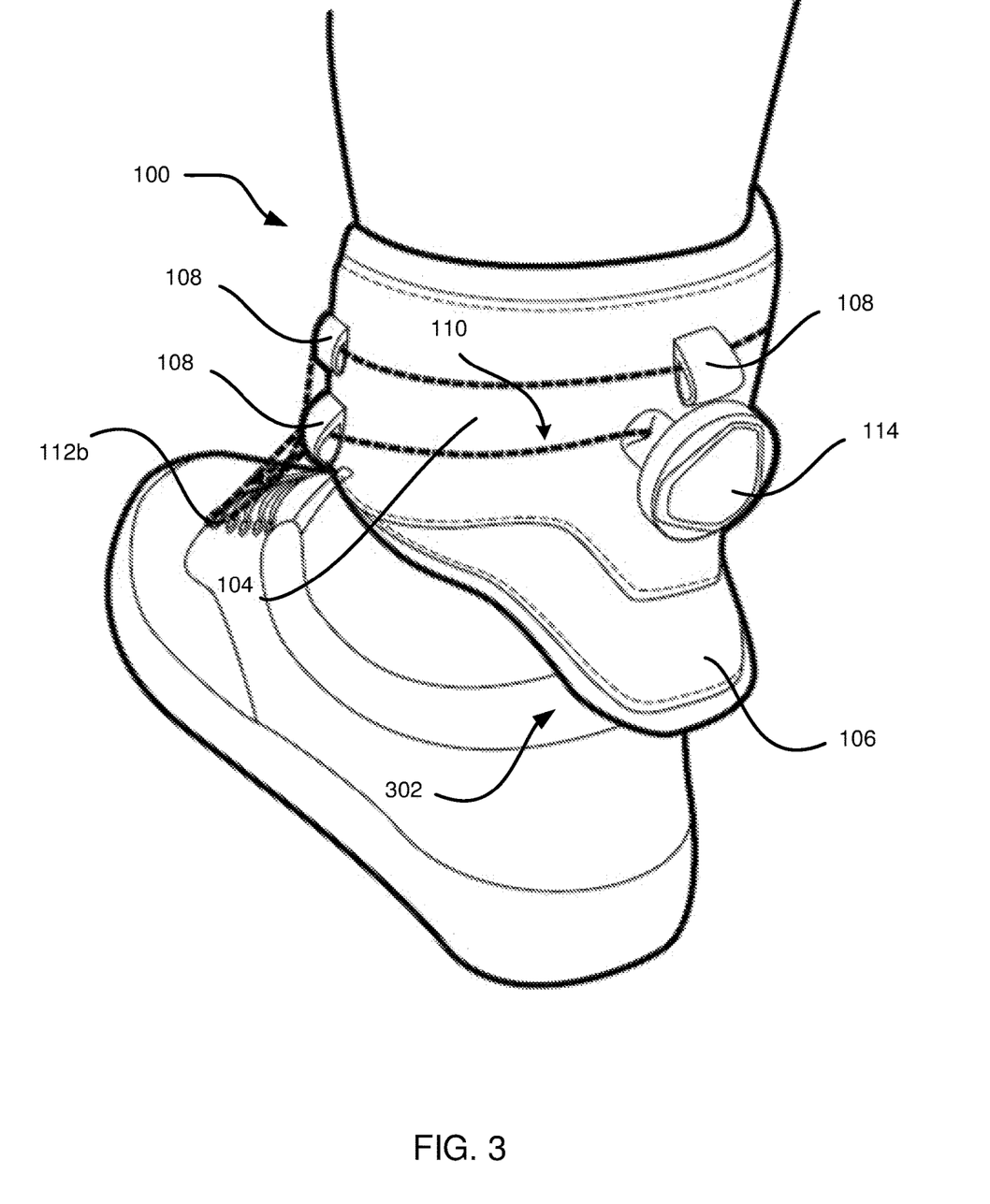
FIG. 3 is a top, rear perspective view of an orthosis brace in use by a user and attached to the user's lower leg, according to one embodiment.
Figure 4:
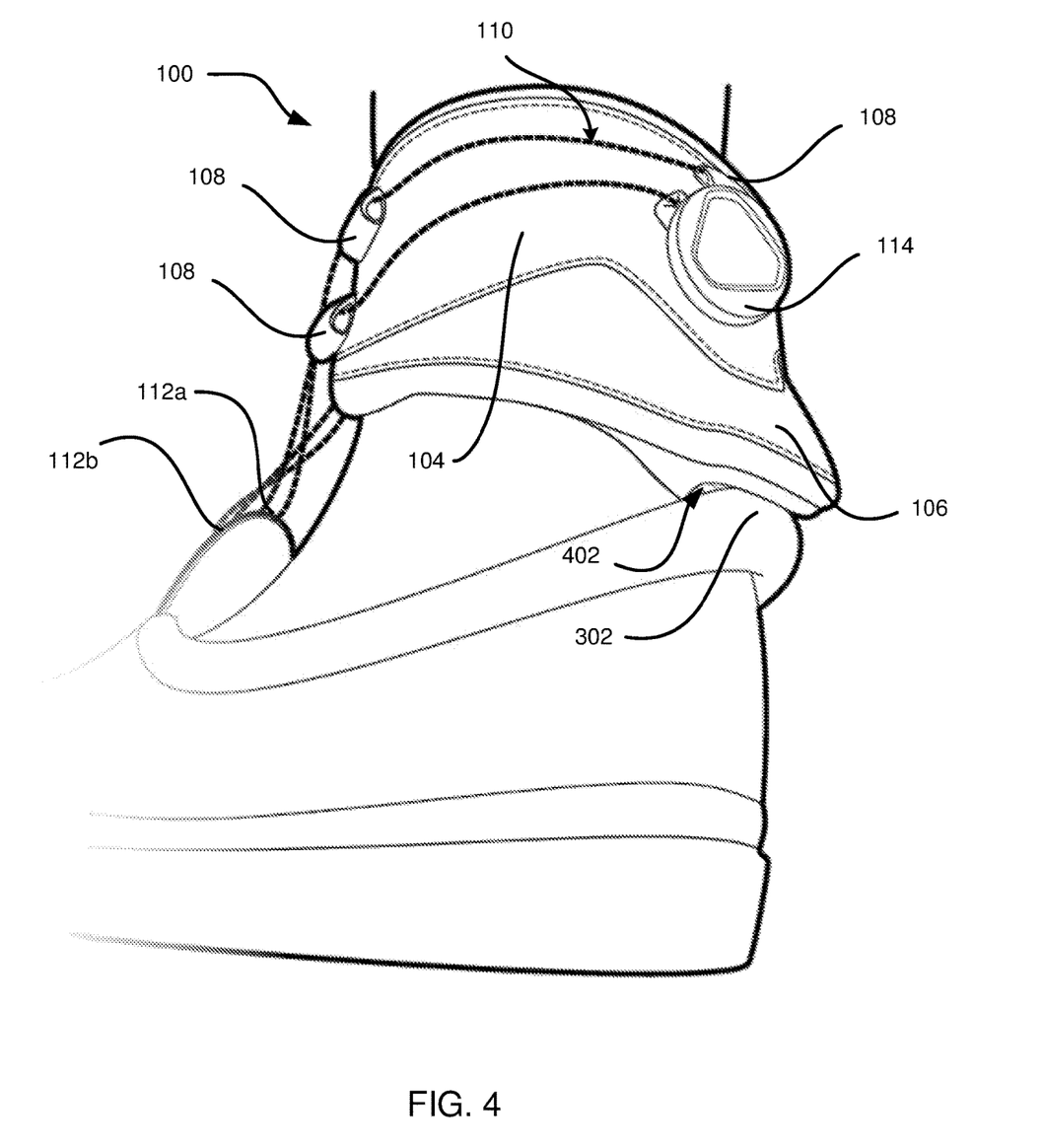
FIG. 4 is a bottom, rear perspective view of an orthosis brace in use by a user and attached to the user's lower leg, according to one embodiment.

The lace 110 includes a first shoe connector 112a and a second shoe connector 112b (may collectively be referred to as shoe connectors 112). The shoe connectors 112 are configured to attach the orthosis brace 100 to a shoe or other footwear. The shoe connectors 112 may comprise a loop in the lace 110 as illustrated in FIG. 1. In alternative embodiments, the shoe connectors 112 may include a fastener attached to the lace 110 such as a snap, knot, hook, button, latch, and so forth. The shoe connectors 112 provide a means to removably attach the orthosis brace 100 to a shoe or other footwear being worn by a user. In an embodiment, the shoe connectors 112 comprise a loop in the lace 110 configured to be looped around a lace, eyelet, button, or other device of the user's footwear. FIGS. 3-4 illustrate an implementation wherein the orthosis brace 100 is attached to a user's footwear.

The reel-based fastener 114 provides a means to quickly tighten or release the lace 110. In an embodiment, the reel-based fastener 114 comprising a lacing system such as the BOA® Fit System manufactured by BOA®. The reel-based fastener 114 may comprise any suitable lace tightening and loosening system. The reel-based fastener 114 is configured to receive the lace 110 and tighten the tautness of the lace 110 by winding the lace 110 around an internal reel. The reel-based fastener 114 is additionally configured to release the lace 110 and loosen the tautness of the lace 110 by permitting the lace 110 to unwind from the internal reel. The reel-based fastener 114 may be turned manually by a user to quickly tighten or release the lace 110. The reel-based fastener 114 is configured to securely maintain the tautness of the lace 110 when the position of the internal reel has been set.

In an embodiment, the reel-based fastener 114 comprises a locking mechanism for locking the reel and preventing the lace 110 from unwinding from the reel. In an embodiment, the locking mechanism may be engaged by a user by depressing an exterior housing for the reel-based fastener. In the embodiment, the user may similarly disengage the lock by pulling out the exterior housing. In an embodiment, the user may rotate the reel-based fastener to increase or decrease the tautness of the lace 110 only when the locking mechanism is disengaged.

In an embodiment, the reel-based fastener 114 is configured to maintain the tautness of the lace 110 when the support 102 is wrapped around the lower leg of the user and one or more of the first shoe connector 112a or the second shoe connector 112b is secured to a shoe worn by the user. When the device 100 is in use and secured to the user's shoe, the reel-based fastener 114 can increase, decrease, or maintain the tautness of the lace 110. In an embodiment, a user may decrease the tautness of the lace 110 by turning the exterior housing the reel-based fastener 114 in a counterclockwise direction and thereby unwinding the reel. In an embodiment, the user may increase the tautness of the lace 110 by turning the exterior housing of the reel-based fastener in a clockwise direction and thereby winding the reel.

Figure 2:
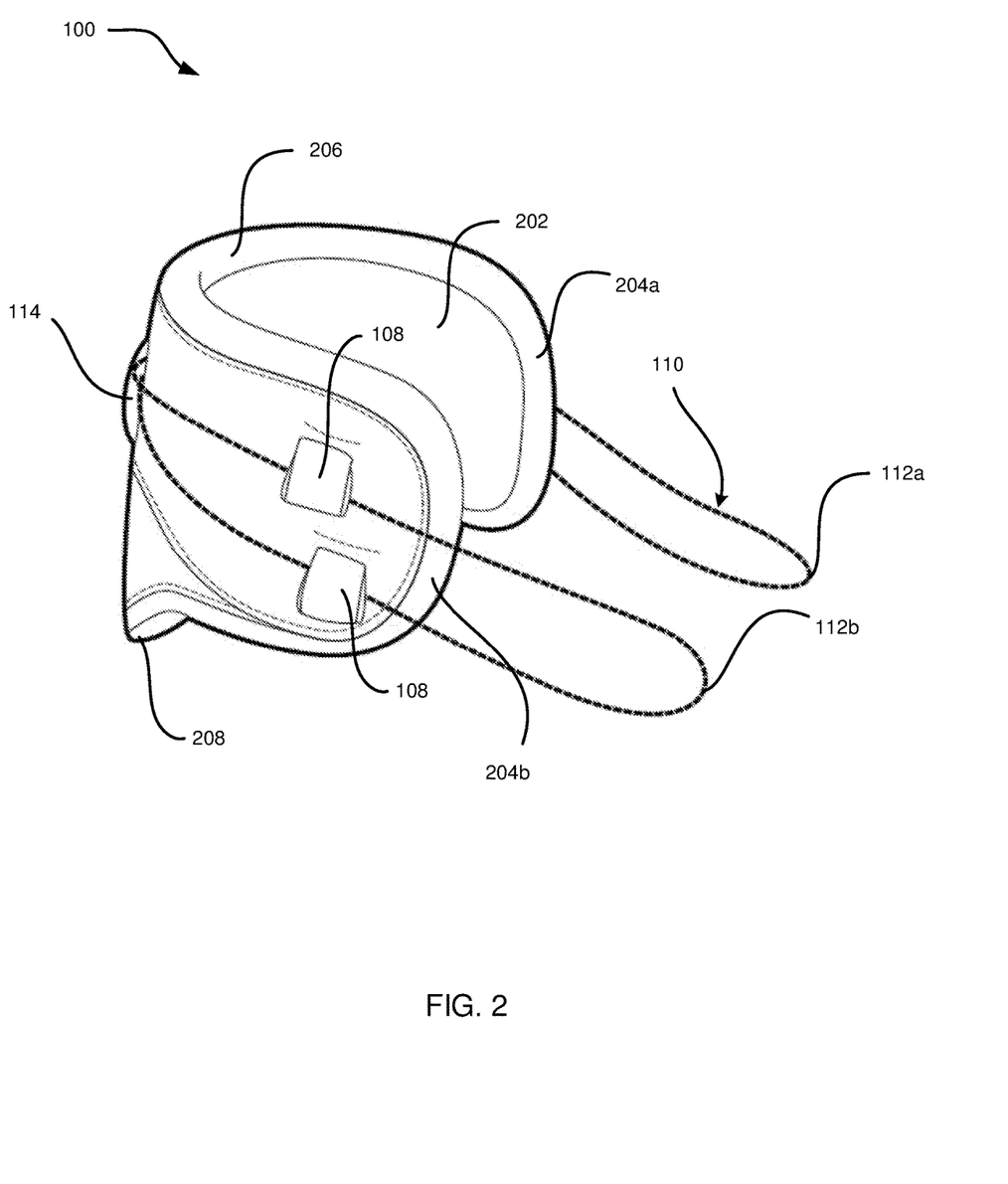
FIG. 2 is a side perspective view of an orthosis brace for correcting foot drop and other conditions that may be alleviated by adjusting an angle of the foot relative to the lower leg, according to one embodiment.

FIG. 2 is a perspective side view of the orthosis brace 100. As illustrated in FIG. 2, the lace 110 may wind through the reel-based fastener 114 at a rear portion of the orthosis brace 100, relative to the anterior side of a user's body when being worn by the user. The lace 110 may then wrap around the sides of the orthosis brace 100 and terminate with loops forming the shoe connectors 112 at the front of the orthosis brace 100, relative to the anterior side of the user's body when being worn by the user.

In an embodiment, the orthosis brace 100 includes inner padding 202 located on an interior side of the orthosis brace 100, relative to the lace 110 on the exterior side of the orthosis brace 100. The inner padding 202 may provide support and comfort to a user when the orthosis brace 100 is securely wrapped around a user's ankle. The inner padding 202 may additionally provide support to reduce the risk the user will experience friction or abrasions that could harm the user's skin when the orthosis brace 100 is being worn.

In an embodiment, the support 102 includes a first support edge 204a and a second support edge 204b (may collectively be referred to herein as the support edges 204). The support 102 further includes an upper edge 206 and a bottom edge 208. The upper edge 206 may constitute the highest point of the device 100 when the device 100 is in use and installed on a user's lower leg. The lower edge 208 may constitute the lowest point of the device 100 and may be configured to rest on or brace against a counter of the user's footwear. In an embodiment, if the support 102 were to be laid out flat, then one side of the support 102 would constitute the first support edge 204a and the opposite side of the support 102 would constitute the second support edge 204b. Further, one long side of the support 102 would constitute the upper edge 206 and the opposite side of the support 102 would constitute the lower edge 208.

The upper edge 206 and the lower edge 208 may comprise a shape and curvature approximately matching the shape and curvature of the user's lower leg. The first support edge 204a and the second support edge 204b may terminate at the anterior side of the user's lower leg when the device 100 is installed on the user's leg and the support 102 is wrapped around the ankle portion of the user's leg. In an embodiment, the first support edge 204a and the second support edge 204b do not touch to complete an elliptical shape. Instead, the first support edge 204a and the second support edge 204b may be located at some point on the anterior side of the user's lower leg and provide an open space on the anterior side of the user's lower leg where the device 100 is not touching the user's leg. This can be beneficial to the user to provide the user with additional space and flexibility for altering the angle of the user's lower leg relative to the user's foot when walking, standing, or moving the foot.

FIG. 3 illustrates a perspective rear view of the orthosis brace 100 when being worn by a user. As shown in FIG. 3, the orthosis brace 100 may be secured to a shoe with the shoe connector 112b. In an embodiment, the shoe connectors 112 cross across the front of the user's footwear to wrap the orthosis brace 100 more securely around the user's ankle. In an alternative embodiment, the shoe connectors 112 do not cross over the front of the user's footwear and instead connect directly outward relative to the orthosis brace 100. Further as illustrated, the orthosis brace 100 may wrap around the user's lower leg such that the counter support portion 106 is located near the counter 302 of the user's footwear. Additionally, the ankle support portion 104 wraps around the posterior side of the user's ankle near the user's Achilles tendon.

In an embodiment, the counter support portion 106 contacts and presses against the counter 302 of the user's footwear. In such an embodiment, the counter 302 of the user's footwear acts as a limiting factor against downward drift of the orthosis brace 100. The counter 302 of the user's footwear, along with the counter support portion 106 of the orthosis brace 100, prevents the orthosis brace 100 from sliding down the user's leg. In an embodiment, the counter support portion 106 includes a thick padding, brace, or other structure configured to press against the counter 302 of the user's footwear (see the footwear counter brace 402 first illustrated in FIG. 4).

The orthosis brace 100 wraps around the posterior side of the user's lower leg and further attaches to the user's footwear. The tautness of the orthosis brace 100 may be altered by the user by winding the reel-based fastener 114 to tighten or release the lace 110. The orthosis brace 100 leverages the support of the user's lower leg along with the support of the user's footwear to lift the user's foot. The orthosis brace 100 thereby alleviates symptoms of foot drop that may be experienced by the user. The user may adjust the degree to which the orthosis brace 100 lifts the user's foot by altering the tautness of the lace 110 by winding the reel-based fastener 114.

FIG. 4 illustrates a perspective underside view of the orthosis brace 100 being worn by a user. FIG. 4 illustrates an embodiment wherein the counter support portion 106 of the support 102 includes a footwear counter brace 402. The footwear counter brace 402 may comprise a channel, cutout, notch, or curvature configured to match the curvature of the counter 302 of the user's footwear. The footwear counter brace 402 is configured to brace against the counter 302 of the user's footwear to support the orthosis brace 100 and further to increase the comfort of wearing the orthosis brace 100 for the user. The footwear counter brace 402 may be specifically shaped and sized for certain types of footwear, for example, for athletic footwear, for specialty orthotic footwear, for leisure footwear, and so forth. In an embodiment, the footwear counter brace 402 is personalized to the user's selected footwear. In an embodiment, the footwear counter brace 402 is adjustable such that it can be used with different types of footwear. In an embodiment, the footwear counter brace 402 is constructed of a semi-rigid foam or padded material configured to press against the counter 302 of the user's footwear. In an embodiment, the footwear counter brace 402 comprises a rigid frame constructed of metal, polycarbonate, wood, or some other rigid material. The footwear counter brace 402 may press against the counter 302 of the user's footwear such that the user's footwear acts as a limiting factor to prevent the orthosis brace 100 from sliding down the user's leg.

Figure 5:
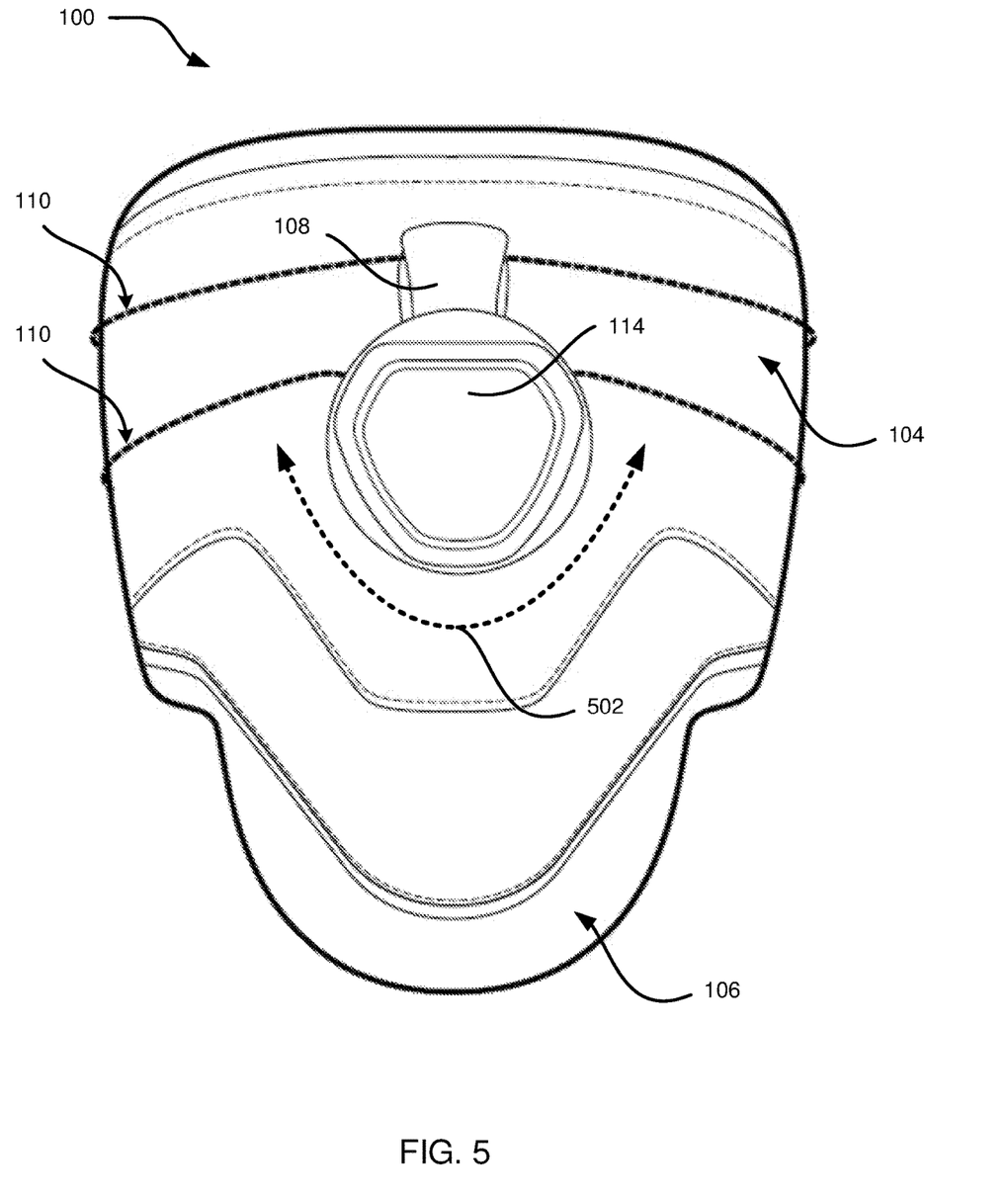
FIG. 5 is a back view of an orthosis brace for correcting foot drop and other conditions that may be alleviated by adjusting an angle of the foot relative to the lower leg, according to one embodiment.

FIG. 5 illustrates a back view of the orthosis brace 100, wherein the rear side of the orthosis brace is the side located at the posterior side of a user's body when the orthosis brace 100 is in use. FIG. 5 further illustrates a straight-on view of the reel-based fastener 114 that may be secured to the back side of the orthosis brace 100. The dotted line 502 indicates that the reel-based fastener 114 may be turned clockwise or counter-clockwise to alter the tautness of the lace 110 wound within the reel-based fastener 114. In an embodiment, a user may turn the reel-based fastener 114 clockwise to wind the lace 110 within the reel-based fastener 114 and thereby tighten the orthosis brace 100. In an embodiment, the user may additionally turn the reel-based fastener 114 counter-clockwise to unwind the lace 110 within the reel-based fastener 114 and thereby loosen the orthosis brace 100. The opposite may be true, and it should be appreciated that the reel-based fastener 114 may be configured to wind and unwind the lace 110 based on either suitable turning direction.

Figure 6:
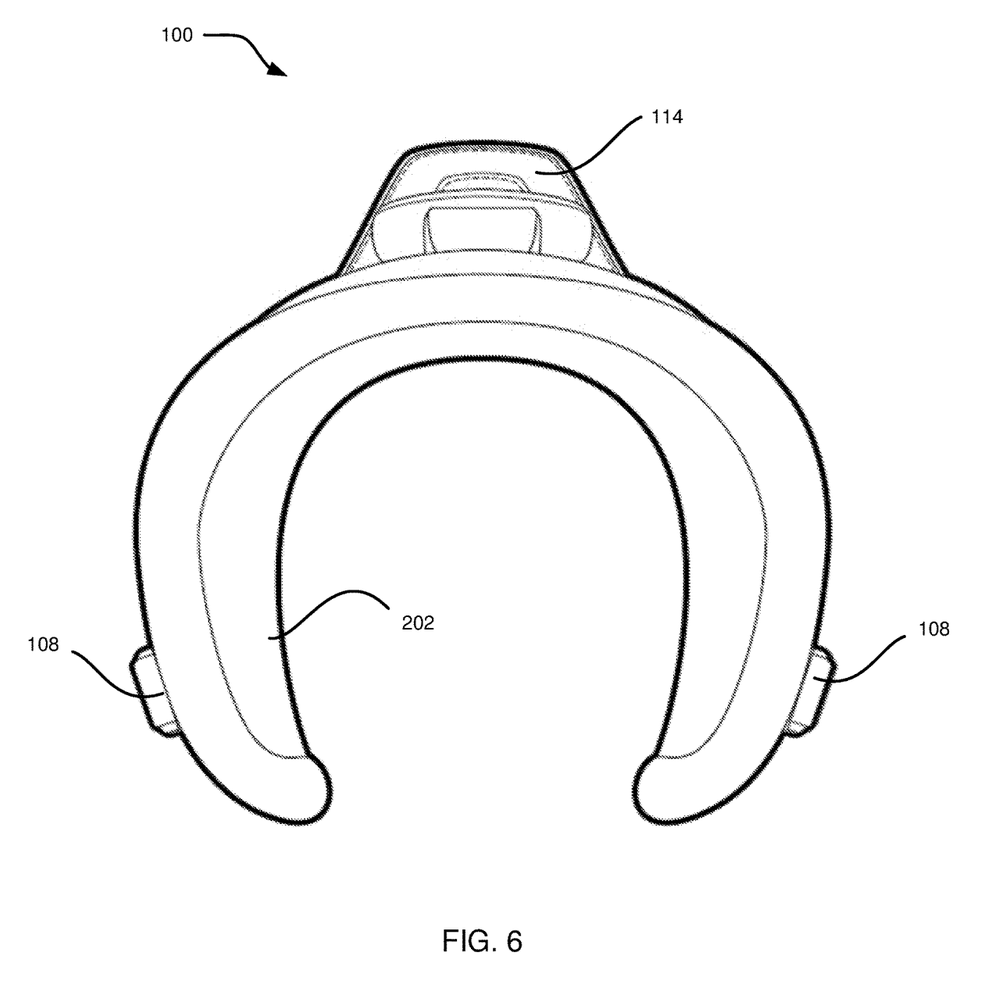
FIG. 6 is an aerial top-down view of an orthosis brace for correcting foot drop and other conditions that may be alleviated by adjusting an angle of the foot relative to the lower leg, according to one embodiment.
Figure 7:
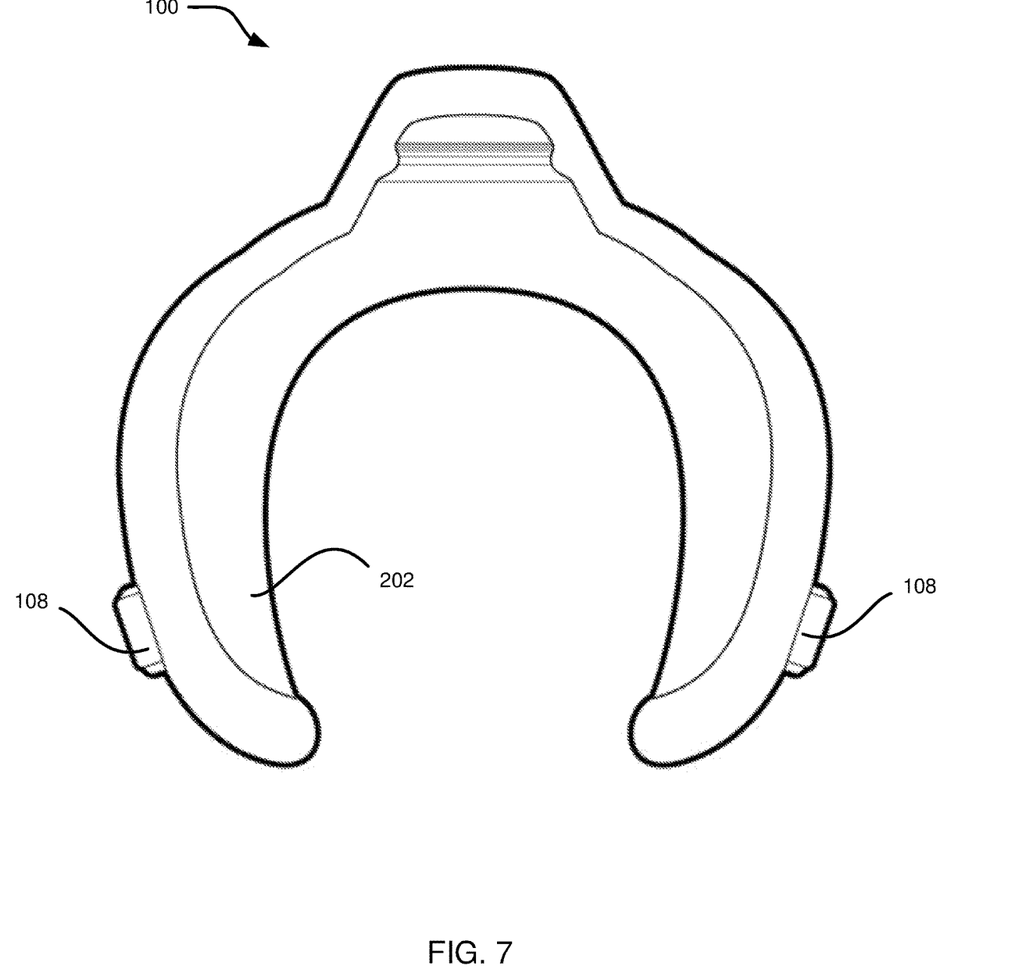
FIG. 7 is an underside view of an orthosis brace for correcting foot drop and other conditions that may be alleviated by adjusting an angle of the foot relative to the lower leg, according to one embodiment.

FIG. 6 illustrates an aerial top-down view of the orthosis brace 100 and FIG. 7 illustrates an underside view of the orthosis brace 100. As shown, the orthosis brace 100 may comprise a curvature configured for wrapping around a user's lower leg. This curvature may be permanently or semi-permanently formed by a rigid, semi-rigid, or semi-malleable material. In an example embodiment, the support 102 comprises a semi-rigid inner material that can be shaped around the user's lower leg and then maintains that shape unless forcibly reformed into a new shape. In an alternative example embodiment, the support 102 comprises a rigid inner material that is irreversibly shaped to the user's lower leg. The orthosis brace 100 may be personalized to a certain user or may be performed to work with all users, or with all users with certain ranges of leg sizes. For example, the orthosis brace 100 may be constructed in "small," "medium," and "large" sizes, as needed, to accommodate different users.

Figure 8:
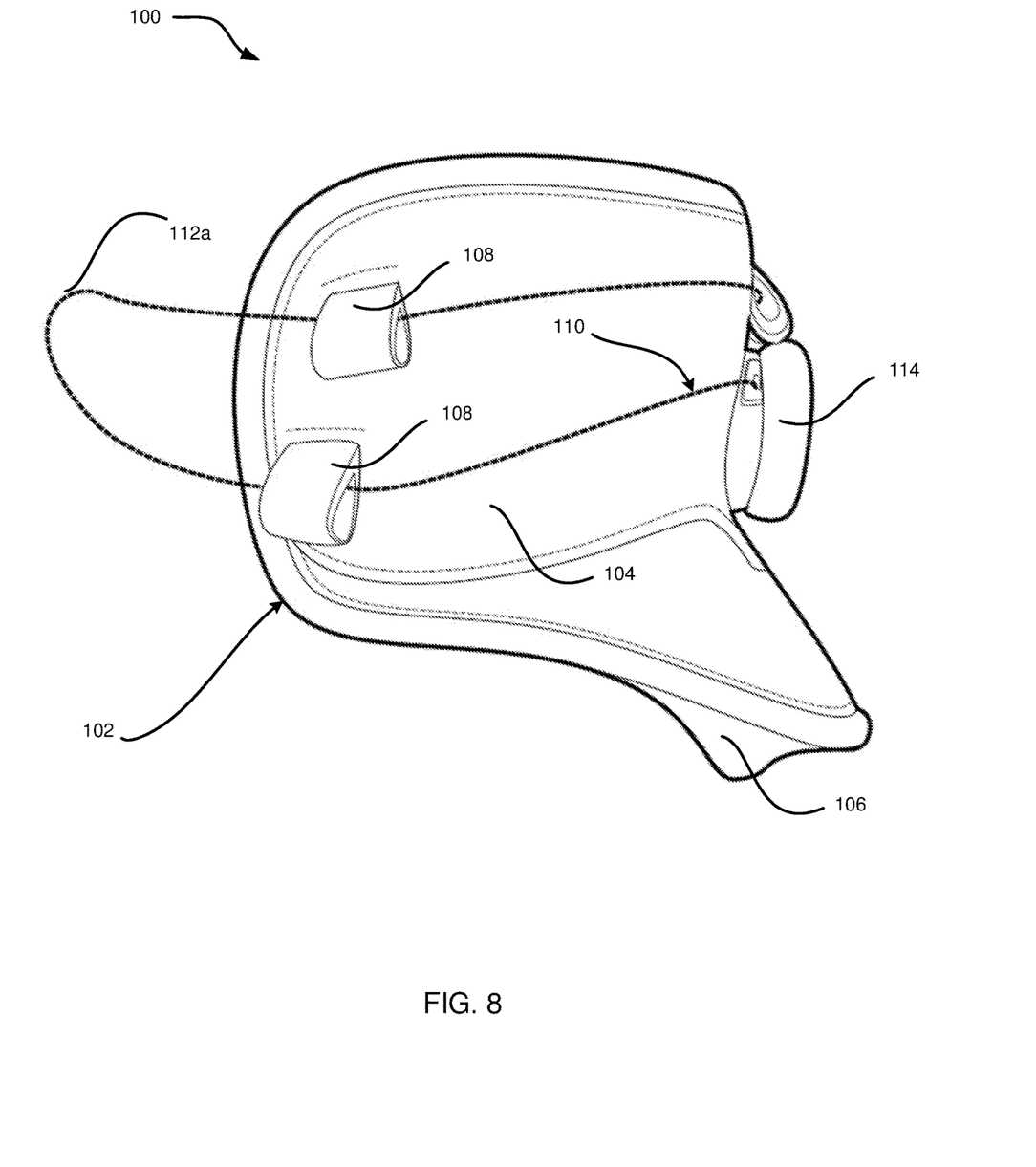
FIG. 8 is a perspective side view of an orthosis brace for correcting foot drop and other conditions that may be alleviated by adjusting an angle of the foot relative to the lower leg, according to one embodiment.
Figure 9:
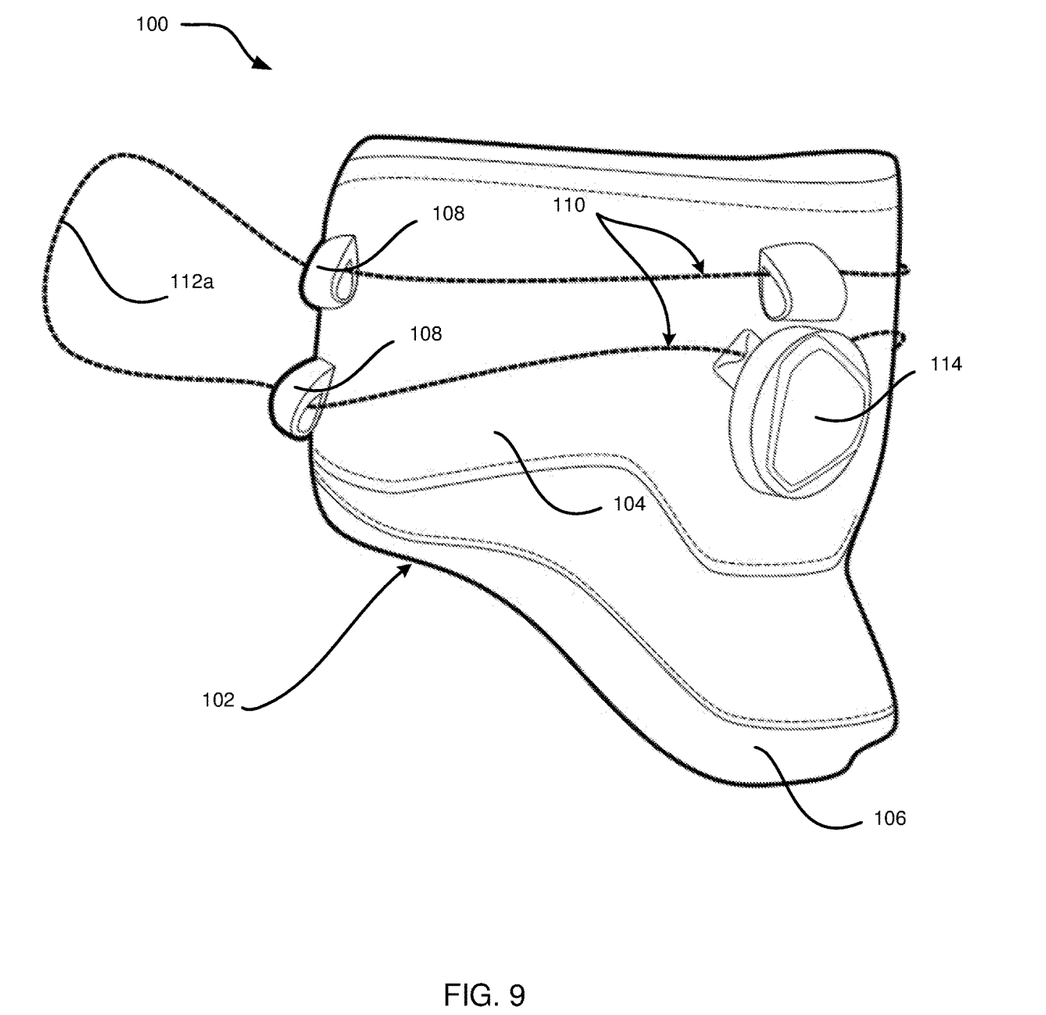
FIG. 9 is a perspective side-back view of an orthosis brace for correcting foot drop and other conditions that may be alleviated by adjusting an angle of the foot relative to the lower leg, according to one embodiment.

FIGS. 8 and 9 illustrate a perspective side views of the orthosis brace 100. As shown, in an embodiment, the lace 110 comprises a single string or twine the terminates inside the reel-based fastener 114. The reel-based fastener 114 secures each of the two ends of the single lace 110 such that the lace 110 forms a continuous loop around the orthosis brace 100. In an embodiment, a first end of the lace 110 is attached to the reel-based fastener and is then fed through two or more lace supports 108 to form the first shoe connector 112. The lace 110 is again fed through two more lace supports 108 on the opposite side of the orthosis brace 100, and then terminates within the reel-based fastener 114. In this embodiment, the tightness of the orthosis brace 100 can quickly be altered by winding or unwinding the reel-based fastener 114.

EXAMPLES

The following examples pertain to further embodiments.

Example 1 is a device. The device includes a support configured to wrap around at least a portion of a lower leg of a user. The device includes a lace support attached to the support and configured to receive a lace. The device includes a reel-based fastener attached to the support, wherein the reel-based fastener comprises a reel for receiving the lace and adjusting a tautness of the lace.

Example 2 is a device as in Example 1, wherein the support comprises an ankle support portion configured to wrap around a posterior side of the lower leg of the user at or near an ankle of the user.

Example 3 is a device as in any of Examples 1-2, wherein the support further comprises a counter support portion attached to the ankle support portion, wherein the counter support portion is distal relative to the ankle support portion when the device is secured to the lower leg of the user.

Example 4 is a device as in any of Examples 1-3, wherein the counter support portion extends outward relative to the lower leg of the user when the device is secured to the lower leg of the user such that the counter support portion provides sufficient space for a counter of the user's footwear.

Example 5 is a device as in any of Examples 1-4, wherein the lace comprises a single line comprising a first end and a second end, and wherein each of the first end and the second end of the lace is attached to the reel-based fastener.

Example 6 is a device as in any of Examples 1-5, wherein the reel-based fastener is configured to be rotated by a user, and wherein rotating the reel-based fastener causes the lace to one or more of: wind on to the reel and increase the tautness of the lace; or unwind from the reel and decrease the tautness of the lace.

Example 7 is a device as in any of Examples 1-6, wherein the lace support comprises a plurality of lace supports for receiving and securing the lace to the device.

Example 8 is a device as in any of Examples 1-7, wherein: the lace comprises a first shoe connector and a second shoe connector; each of the first shoe connector and the second shoe connector comprises a shoe fastener for securing the device to a footwear of the user; and the shoe fastener comprises one or more of a loop formed by the lace, a hook, a snap, a knot, a button, or a latch.

Example 9 is a device as in any of Examples 1-8, wherein the support comprises a counter support portion, and wherein the counter support portion comprises a footwear counter brace configured to brace against a counter of the user's footwear, wherein the footwear counter brace comprises a curvature approximately inverse to a curvature of the counter of the user's footwear.

Example 10 is a device as in any of Examples 1-9, wherein the support comprises a first support edge and a second support edge, and wherein the support is configured to wrap around a posterior portion of the lower leg of the user such that each of the first support edge and the second support edge terminate at an anterior portion of the lower leg of the user.

Example 11 is a device as in any of Examples 1-10, wherein the first support edge does not come in contact with the second support edge when the device is worn by the user such that the support wraps around a posterior portion of the lower leg of the user and provides an open space at the anterior portion of the lower leg of the user.

Example 12 is a device as in any of Examples 1-11, wherein the lace support comprises a plurality of loops configured for releasably receiving the lace, wherein the plurality of loops comprise one or more of: a first loop located near the first support edge; a second loop located near the first support edge; a first loop located near the second support edge; a second loop located near the second support edge; and a posterior loop located near the reel-based fastener on a posterior side of the device, wherein the posterior side of the device is located at a posterior side of the user when the device is worn by the user.

Example 13 is a device as in any of Examples 1-12, wherein: the lace is threaded through the first loop located near the first support edge and the second loop located near the first support edge such that the lace forms a first shoe connector loop at the first support edge; and the lace is threaded through the first loop located near the second support edge and the second loop located near the second support edge such that the lace forms a second shoe connector loop at the second support edge.

Example 14 is a device as in any of Examples 1-13, wherein each of the first shoe connector loop and the second shoe connector loop is configured to releasably secure the device to a shoe worn by the user.

Example 15 is a device as in any of Examples 1-14, wherein the support comprises a rigid inner frame and an outer padding, wherein the rigid inner frame comprises a curvature approximately matching an outer curvature of the lower leg of the user.

Example 16 is a device as in any of Examples 1-15, wherein the lace support comprises four or more lace supports attached to the support, and wherein each of the four or more lace supports comprises a loop configured for releasably receiving the lace therein.

Example 17 is a device as in any of Examples 1-16, wherein the device is configured to alleviate foot drop experienced by the user.

Example 18 is a device as in any of Examples 1-17, wherein the support comprises sufficient rigidity to resist collapsing when the device is worn by the user and the user is walking.

Example 19 is a device as in any of Examples 1-18, wherein: the tautness of the lace is increased or decreased by the reel-based fastener when the support is wrapped around the lower leg of the user and the lace is secured to a shoe worn by the user; the reel-based fastener is configured to increase the tautness of the lace when the reel is rotated in a clockwise direction; and the reel-based fastener is configured to decrease the tautness of the lace when the reel is rotated in a counter-clockwise direction.

Example 20 is a device as in any of Examples 1-19, wherein the reel-based fastener comprises a locking mechanism for locking the reel and preventing the lace from unwinding from the reel.

Example 21 is a system. The system includes a shoe comprising shoe counter. The system includes a support configured to wrap around at least a portion of a lower leg of a user. The system includes a lace support attached to the support and configured to receive a lace. The system includes a reel-based fastener attached to the support, wherein the reel-based fastener comprises a reel for receiving the lace and adjusting a tautness of the lace.

Example 22 is a system as in Example 21, wherein the support comprises an ankle support portion configured to wrap around a posterior side of the lower leg of the user at or near an ankle of the user.

Example 23 is a system as in any of Examples 21-22, wherein the support further comprises a counter support portion attached to the ankle support portion, wherein the counter support portion is distal relative to the ankle support portion when the device is secured to the lower leg of the user.

Example 24 is a system as in any of Examples 21-23, wherein the counter support portion extends outward relative to the lower leg of the user when the device is secured to the lower leg of the user such that the counter support portion provides sufficient space for the shoe counter of the shoe.

Example 25 is a system as in any of Examples 21-24, wherein the lace comprises a single line comprising a first end and a second end, and wherein each of the first end and the second end of the lace is attached to the reel-based fastener.

Example 26 is a system as in any of Examples 21-25, wherein the reel-based fastener is configured to be rotated by a user, and wherein rotating the reel-based fastener causes the lace to one or more of: wind on to the reel and increase the tautness of the lace; or unwind from the reel and decrease the tautness of the lace.

Example 27 is a system as in any of Examples 21-26, wherein the lace support comprises a plurality of lace supports for receiving and securing the lace to the device.

Example 28 is a system as in any of Examples 21-27, wherein: the lace comprises a first shoe connector and a second shoe connector; each of the first shoe connector and the second shoe connector comprises a shoe fastener for securing the device to a footwear of the user; and the shoe fastener comprises one or more of a loop formed by the lace, a hook, a snap, a knot, a button, or a latch.

Example 29 is a system as in any of Examples 21-28, wherein the support comprises a counter support portion, and wherein the counter support portion comprises a footwear counter brace configured to brace against the shoe counter of the shoe, wherein the footwear counter brace comprises a curvature approximately inverse to a curvature of the shoe counter of the shoe.

Example 30 is a system as in any of Examples 21-29, wherein the support comprises a first support edge and a second support edge, and wherein the support is configured to wrap around a posterior portion of the lower leg of the user such that each of the first support edge and the second support edge terminate at an anterior portion of the lower leg of the user.

Example 31 is a system as in any of Examples 21-30, wherein the first support edge does not come in contact with the second support edge when the device is worn by the user such that the support wraps around a posterior portion of the lower leg of the user and provides an open space at the anterior portion of the lower leg of the user.

Example 32 is a system as in any of Examples 21-31, wherein the lace support comprises a plurality of loops configured for releasably receiving the lace, wherein the plurality of loops comprise one or more of: a first loop located near the first support edge; a second loop located near the first support edge; a first loop located near the second support edge; a second loop located near the second support edge; and a posterior loop located near the reel-based fastener on a posterior side of the device, wherein the posterior side of the device is located at a posterior side of the user when the device is worn by the user.

Example 33 is a system as in any of Examples 21-32, wherein: the lace is threaded through the first loop located near the first support edge and the second loop located near the first support edge such that the lace forms a first shoe connector loop at the first support edge; and the lace is threaded through the first loop located near the second support edge and the second loop located near the second support edge such that the lace forms a second shoe connector loop at the second support edge.

Example 34 is a system as in any of Examples 21-33, wherein each of the first shoe connector loop and the second shoe connector loop is configured to releasably secure the device to a shoe worn by the user.

Example 35 is a system as in any of Examples 21-34, wherein the support comprises a rigid inner frame and an outer padding, wherein the rigid inner frame comprises a curvature approximately matching an outer curvature of the lower leg of the user.

Example 36 is a system as in any of Examples 21-35, wherein the lace support comprises four or more lace supports attached to the support, and wherein each of the four or more lace supports comprises a loop configured for releasably receiving the lace therein.

Example 37 is a system as in any of Examples 21-36, wherein the device is configured to alleviate foot drop experienced by the user.

Example 38 is a system as in any of Examples 21-37, wherein the support comprises sufficient rigidity to resist collapsing when the device is worn by the user and the user is walking.

Example 39 is a system as in any of Examples 21-38, wherein: the tautness of the lace is increased or decreased by the reel-based fastener when the support is wrapped around the lower leg of the user and the lace is secured to a shoe worn by the user; the reel-based fastener is configured to increase the tautness of the lace when the reel is rotated in a clockwise direction; and the reel-based fastener is configured to decrease the tautness of the lace when the reel is rotated in a counter-clockwise direction.

Example 40 is a system as in any of Examples 21-39, wherein the reel-based fastener comprises a locking mechanism for locking the reel and preventing the lace from unwinding from the reel.

In the above disclosure, reference has been made to the accompanying drawings, which form a part hereof, and in which is shown by way of illustration specific implementations in which the disclosure may be practiced. It is understood that other implementations may be utilized, and structural changes may be made without departing from the scope of the present disclosure. References in the specification to "one embodiment," "an embodiment," "an example embodiment," etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described.

While various embodiments of the present disclosure have been described above, it should be understood that they have been presented by way of example only, and not limitation. It will be apparent to persons skilled in the relevant art that various changes in form and detail can be made therein without departing from the spirit and scope of the disclosure. Thus, the breadth and scope of the present disclosure should not be limited by any of the above-described exemplary embodiments but should be defined only in accordance with the following claims and their equivalents. The foregoing description has been presented for the purposes of illustration and description. It is not intended to be exhaustive or to limit the disclosure to the precise form disclosed. Many modifications and variations are possible in light of the above teaching. Further, it should be noted that any or all of the aforementioned alternate implementations may be used in any combination desired to form additional hybrid implementations of the disclosure.

Further, although specific implementations of the disclosure have been described and illustrated, the disclosure is not to be limited to the specific forms or arrangements of parts so described and illustrated. The scope of the disclosure is to be defined by the claims appended hereto, any future claims submitted here and in different applications, and their equivalents.

What is claimed is:

1. A device comprising:
   a support comprising an upper edge and a lower edge configured to wrap around at least a portion of a lower leg of a user, wherein the upper edge and the lower edge comprise a shape and a curvature approximately matching a shape and a curvature of the lower leg of the user;
   a reel-based fastener attached to a posterior portion of the support;
   a lace configured to wind through the reel-based fastener; and
   a lace support attached to the support and configured to receive the lace;
   wherein the reel-based fastener comprises a reel for receiving the lace and adjusting a tautness of the lace;
   wherein the support comprises a first support edge and a second support edge;
   wherein the first support edge does not come in contact with the second support edge;
   wherein the lower edge or the upper edge defines at least a portion of a counter support portion, wherein the counter support portion extends outward relative to the reel-based fastener when the device is secured to the lower leg of the user.

2. The device of claim 1, wherein the support comprises an ankle support portion configured to wrap around a posterior side of the lower leg of the user at or near an ankle of the user.

3. The device of claim 2, wherein counter support portion is attached to the ankle support portion, and wherein the counter support portion is distal relative to the ankle support portion when the device is secured to the lower leg of the user.

4. The device of claim 3, wherein the counter support portion extends outward relative to the lower leg of the user when the device is secured to the lower leg of the user such that the counter support portion provides sufficient space for a counter of the user's footwear.

5. The device of claim 1, wherein the lace comprises a single line comprising a first end and a second end, and wherein each of the first end and the second end of the lace is attached to the reel-based fastener.

6. The device of claim 5, wherein the reel-based fastener is configured to be rotated by a user, and wherein rotating the reel-based fastener causes the lace to one or more of:
   wind on to the reel and increase the tautness of the lace; or
   unwind from the reel and decrease the tautness of the lace.

7. The device of claim 1, wherein the lace support comprises a plurality of lace supports for receiving and securing the lace to the device.

8. The device of claim 1, wherein:
   the lace comprises a first shoe connector and a second shoe connector;
   each of the first shoe connector and the second shoe connector comprises a shoe fastener for securing the device to a footwear of the user; and
   the shoe fastener comprises one or more of a loop formed by the lace, a hook, a snap, a knot, a button, or a latch.

9. The device of claim 1, wherein the support comprises a counter support portion, and wherein the counter support portion comprises a footwear counter brace configured to brace against a counter of the user's footwear, wherein the footwear counter brace comprises a curvature approximately inverse to a curvature of the counter of the user's footwear.

10. The device of claim 1, wherein the support is configured to wrap around a posterior portion of the lower leg of the user such that each of the first support edge and the second support edge terminate at an anterior portion of the lower leg of the user.

11. The device of claim 10, wherein when the device is worn by the user the support wraps around a posterior portion of the lower leg of the user and provides an open space at the anterior portion of the lower leg of the user.

12. The device of claim 10, wherein the lace support comprises a plurality of loops configured for releasably receiving the lace, wherein the plurality of loops comprise one or more of:
- a first loop located near the first support edge;
- a second loop located near the first support edge;
- a first loop located near the second support edge;
- a second loop located near the second support edge; and
- a posterior loop located near the reel-based fastener on a posterior side of the device, wherein the posterior side of the device is located at a posterior side of the user when the device is worn by the user.

13. The device of claim 12, wherein:
the lace is threaded through the first loop located near the first support edge and the second loop located near the first support edge such that the lace forms a first shoe connector loop at the first support edge;
the lace is threaded through the first loop located near the second support edge and the second loop located near the second support edge such that the lace forms a second shoe connector loop at the second support edge.

14. The device of claim 13, wherein each of the first shoe connector loop and the second shoe connector loop is configured to releasably secure the device to a shoe worn by the user.

15. The device of claim 1, wherein the support comprises a rigid inner frame and an outer padding, wherein the rigid inner frame comprises a curvature approximately matching an outer curvature of the lower leg of the user.

16. The device of claim 1, wherein the lace support comprises four or more lace supports attached to the support, and wherein each of the four or more lace supports comprises a loop configured for releasably receiving the lace therein.

17. The device of claim 1, wherein the device is configured to alleviate foot drop experienced by the user.

18. The device of claim 1, wherein the support comprises sufficient rigidity to resist collapsing when the device is worn by the user and the user is walking.

19. The device of claim 1, wherein:
the tautness of the lace is increased or decreased by the reel-based fastener when the support is wrapped around the lower leg of the user and the lace is secured to a shoe worn by the user;
the reel-based fastener is configured to increase the tautness of the lace when the reel is rotated in a clockwise direction; and
the reel-based fastener is configured to decrease the tautness of the lace when the reel is rotated in a counter-clockwise direction.

20. The device of claim 1, wherein the reel-based fastener comprises a locking mechanism for locking the reel and preventing the lace from unwinding from the reel.

\* \* \* \* \*